(12) United States Patent
Reynolds

(10) Patent No.: US 9,295,628 B2
(45) Date of Patent: *Mar. 29, 2016

(54) STABILIZED CALCIUM PHOSPHATE COMPLEXES

(71) Applicant: The University of Melbourne, Parkville (AU)

(72) Inventor: Eric Charles Reynolds, Melbourne (AU)

(73) Assignee: The University of Melbourne, Parkville, Victoria (AU)

(*) Notice: Subject to any disclaimer, the term of this patent is extended or adjusted under 35 U.S.C. 154(b) by 52 days.

This patent is subject to a terminal disclaimer.

(21) Appl. No.: 14/077,713

(22) Filed: Nov. 12, 2013

(65) Prior Publication Data

US 2014/0079650 A1    Mar. 20, 2014

Related U.S. Application Data

(63) Continuation of application No. 11/720,285, filed as application No. PCT/AU2005/001781 on Nov. 24, 2005, now Pat. No. 8,609,071.

(30) Foreign Application Priority Data

Nov. 25, 2004 (AU) ............................. 2004906762

(51) Int. Cl.
```
A61K 8/21    (2006.01)
A61K 8/64    (2006.01)
A61K 8/20    (2006.01)
A61K 8/24    (2006.01)
A61Q 11/00   (2006.01)
C07K 7/06    (2006.01)
A61K 8/69    (2006.01)
A61K 38/00   (2006.01)
```

(52) U.S. Cl.
CPC ... *A61K 8/64* (2013.01); *A61K 8/20* (2013.01); *A61K 8/24* (2013.01); *A61K 8/69* (2013.01); *A61Q 11/00* (2013.01); *C07K 7/06* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,522,805 A | 6/1985 | Gordan | |
| 5,015,628 A | 5/1991 | Reynolds | |
| 6,056,930 A | 5/2000 | Tung | |
| 6,780,844 B1 * | 8/2004 | Reynolds | A61K 8/64 424/49 |
| 7,312,193 B2 | 12/2007 | Reynolds | |
| 7,491,694 B2 | 2/2009 | Reynolds et al. | |
| 2002/0028251 A1 | 3/2002 | Okay | |
| 2005/0063922 A1 | 3/2005 | Reynolds et al. | |

FOREIGN PATENT DOCUMENTS

| | | |
|---|---|---|
| EP | 1 525 878 A1 | 4/2005 |
| JP | 10-290682 A | 11/1998 |
| JP | 11-310599 A | 11/1999 |
| JP | 3742523 | 11/1999 |
| JP | 2004-215521 A | 8/2004 |
| WO | 87/07615 A1 | 12/1987 |
| WO | 93/03707 A1 | 3/1993 |
| WO | 94/00146 A1 | 1/1994 |
| WO | 98/40406 A1 | 9/1998 |
| WO | 00/57892 A1 | 10/2000 |
| WO | 01/44106 A1 | 6/2001 |
| WO | 02/094204 A1 | 11/2002 |
| WO | 03/059303 A2 | 7/2003 |
| WO | 03/059304 A1 | 7/2003 |
| WO | 2004/035077 A1 | 4/2004 |
| WO | 2004/054531 A1 | 7/2004 |
| WO | 2006/130913 A1 | 12/2006 |

OTHER PUBLICATIONS

Adamson et al., "The Analysis of Multiple Phosphoseryl-Containing Casein Peptides Using Capillary Zone Electrophoresis"; J. Chromatogr.; 646(2):391-396. (Sep. 3, 1993).

Adamson et al., "Characterisation of Tryptic Casein Phosphopeptides Prepared Under Industrially-Relevant Conditions"; Biotec. Bioeng; 45:196-4 (1995).

Adamson et al., "High Performance Capillary Electrophoresis of Casein Phosphopeptides Containing 2-5 Phosphoseryl Residues; Relationship Between Absolute Electrophoretic Mobility and Peptide Charge and Size"; Electrophoresis;.16:525-528 (1995).

Adebayo et al., "Effects of conditioners on microshear bond strength to enamel after carbamide peroxide bleaching and/or casein phosphopeptide-amorphous calcium phosphate (CPP-ACP) treatment"; Journal of Dentistry; 35:862-870 (2007).

Allais, "Karies—Die Therapie"; Journal of Continuing Dental Education; pp. 716-735 English Abstract (Jun. 2007).

Al-Zraikat et al., "Development of glass ionomer cement incorporating casein phosphopetide amorphous phosphate (CPP-ACP) complex"; Australian Dental Journal ADRF Special Research Supplement; 52(4):S4 (2007).

Al-Zraikat et al., "Incorporation of casein-phosphopeptide-amorphous calcium phosphate into glass ionomer cement"; Abstract 0654—84th General Session of the IADR, Brisbane, Australia (Jun. 28-Jul. 1, 2006).

(Continued)

*Primary Examiner* — Craig Ricci
(74) *Attorney, Agent, or Firm* — Merchant & Gould P.C.

(57) ABSTRACT

The present invention relates to a phosphopeptide-stabilized amorphous calcium phosphate and/or amorphous calcium fluoride phosphate complex, wherein the complex is formed at a pH of below 7.0. Methods of making such complexes are also provided. The complexes are useful in dental applications, in particular in dental remineralisation.

11 Claims, No Drawings

(56) References Cited

OTHER PUBLICATIONS

Angmar et al., "Studies on the Ulatrastructure of Dental Enamel"; J. Ultrastructure Research; 8(1-2):12-23 (1963).

Aoba et al., "Dental Fluorosis: Chemistry and Biology"; Crit Rev Oral Biol Med.; 13(2):155-170 (2002).

Ardu et al., "A minimally invasive treatment of severe dental fluorosis"; Quintessence International; 38(6):455-458 (Jun. 2007).

Ardu et al., "Minimally invasive treatment of white spot enamel lesions"; Quintessence International; 38(8):633-636 (Sep. 2007).

Aytepe et al., "Effect of CCP-ACP on oral health of cerebral palsy children"; Abstract 3343, Toronto, Canada. (Jul. 2008).

Bavetta et al., "Protein Factors and Experimental Rat Caries"; Nutr. ; 63:107-117 (1957).

Biesbrock, "Relative anti-caries efficacy of 1100, 1700, 2200, and 2800 ppm fluoride ion in a sodium fluoride dentifrice over 1 year"; Community Dentistry and Oral Epidemiology; 29:382-389 (2001).

Biesbrock et al., "Reversal of Incipient and Radiographic Caries Through the Use of Sodium and Stannous Fluoride Dentifrices in a Clinical Trial"; The Journal of Clinical Dentistry; 9(1):5-10 (Feb. 1998).

Biesbrock et al., "Dose response efficacy of sodium fluoride dentifrice at 9 and 21 months with supervised brushing" ; American Journal of Dentistry; 16(5) (Oct. 2003).

Black et al., "Mottled Teeth: An endemic developmental imperfection of the enamel of the teeth heretofore unknown in the literature of dentistry"; The Dental Cosmos; LVIII(2): 129-156 (Feb. 1916).

Burwell et al., "Quantitative Tubule Occlusion in an In Vitro Remineralization/Demineralization Model"; Abstract 0568, EADR, Dublin, Ireland (2006).

Burwell et al., "Dentifrice Protection Against Dentin Demineralization in an In Vitro Study"; Abstract 1764, IADR, New Orleans, USA. (2007).

Cai et al., "Remineralization of Enamel Subsurface Lesions in Situ by Sugar-Free Lozenges Containing Casein Phosphopeptide-Amorphous Calcium Phosphate"; Aus. Dent. J.; 48(4):240-3. (2003).

Cai et al., "Remineralization by chewing gum containing CPP-ACP and citric acid"; Abstract 190—84th General Session of the IADR, Brisbane, Australia (Jun. 28-Jul. 1, 2006).

Cai et al., "Effect of Addition of Citric Acid and Casein Phosphopeptide-Amorphous Calcium Phosphate to a Sugar-free chewing gum on Enamel Remineralization in Situ"; Caries Research; 41:377-383 (2007).

Carrillo et al., "Nuevos avances tecnológicos en Odontologíaa Conservadora"; La Gaceta Dental; 193:213, 218-219, English Abstract (Jun. 2008).

Chalmers et al., "Minimal Intervention Dentistry in the New Millennium"; DDS, MS. Dentaltown; pp. 54 (Feb 2008).

Chelariu et al., "Nuove prospettive nella prevenzione della carieCongresso Nazionale del Collegio dei Docenti di Odontoiatria Roma"; Poster session, published by "Doctor Os", No. 3, (Mar. 2006). English Abstract (Apr. 5-7, 2006).

Chalmers, "Minimal intervention dentistry: part 1. Strategies for addressing the new caries challenge in older patients"; Journal Can. Dental Association; 72(5):427-433 (Jun. 2006).

Chen et al., "Calcium Release and Mechanical Properties of Experimental Calcium-Releasing Composites"; Abstract 2572, IADR, New Orleans, USA (2007).

Cipolla et al., "Fluoride and Calcium-Phosphate Effects on Fracture Toughness of Bleached Dentin"; Abstract 1032, Toronto, Canada (Jul. 2008).

Coates, "Tooth mousse shows some unexpected beneficial side effects"; Dental Asia (Nov./Dec. 2004).

Cochrane et al., "QLF and TMR analysis of CPP-ACFP remineralized enamel in vitro" ; Abstract 192—84th General Session of the IADR, Brisbane, Australia (Jun.28-Jul. 1, 2006).

Cross et al., "Cation-Dependent Structural Features of Beta-Casein-(1-25)"; Biochem. J.; 356:277-286. (May 15, 2001).

Cross et al., "Structural Studies of the β-Casein Phosphopeptide Bound to Amorphous Calcium Phosphate"; IADR, General Session, Chiba, Abstract 0490, (2001).

Cross et al., "Ultrastructural Studies of the Casein Phosphopeptide-Amorphous Calcium Phosphate Nanoclusters"; IADR, General Session, Chiba, Abstract 0491, (2001).

Cross et al., "NMR Studies of a Novel Calcium, Phosphate and Fluoride Delivery Vehicle—The Multiphosphorylated Peptide Alpha S1-Casein (589-79) Complexed with Amorphous Calcium Fluoride Phosphate"; Biomaterials. Accepted for publication, (Jan. 2004).

Cross et al. "Physicochemical Characterization of Casein Phosphopeptide-Amorphous Calcium Phosphate Nanocomplexes"; The Journal of Biological Chemistry; 280(15):15362-15369 (Apr. 15, 2005).

Cross et al., "Structure and $^{15}$N-Dynamics of casein phosphopeptide-amorphous calcium phosphate nanocomplexes"; 84th General Session of the IADRBrisbane, Australia, Abstract 2534 (Jun. 28-Jul. 1, 2006).

Cross et al., "Casein Phosphopeptides in Oral Health—Chemistry and Clinical Applications"; Current Pharmaceutical Design; 13:793-800 (2007).

Cross et al. "Structural Characterization of anticariogenic casein Phosphopeptide alphas2 casein (46-70) complexed with amorphous calcium phosphate"; Australian Dental Journal ADRF Special Research Supplement; 52(4):S10-S11 (2007).

Cross et al., "Structural Characterization ofβ-Casein(1-25)-ACFP Complex"; Australian Dental Journal ADRF Special Research Supplement; 52(4):S12 (2007).

Cross et al. "Casein Phosphopeptide-Amorphous Calcium Phosphate Nanocomplexes: A Model of the Casini Micelle Core"; Centre for Oral Health Science, School of Dental Science, The University of Melbourne, pp. 1-42 (Aug. 2008).

Curnow et al., "A Randomised Controlled Trial of the Efficacy of Supervised Toothbrushing in High—Caries-Risk Children"; Carie Research; 36:294-300 (2002).

Davies, "A randomized controlled trial of the effectiveness of providing free fluoride toothpaste from the age of 12 months on reducing caries in 5-6 year old children"; Community Dental Health; 19:131-136 (2002).

Deangelis et al., "Molecular of Anticariogenic Casein Phosphopeptide AS2-CN (2-20) NMR Spectroscopy Derived Constraints"; Abstract 2997-82nd General Session of the IADR, Honolulu, Hawaii. (2004).

DenBesten et al., "Biological Mechanisms of Fluorosis and Level and Timing of Systemic Exposure to Fluoride with Respect to Fluorosis"; J. Dent Re; 71(5):1238-1243 (May 1992).

Donovan, "Protocol for the prevention and management of root caries"; Journal Compilation; 20(6):405-411 (2008).

Duckworth, "Oral Fluoride Measurements for Estimation of the Anticaries Efficacy of Fluoride Treatments"; J Dent Res; (Apr. 1992).

Duckworth, "Effects of Mouthwashes of Variable NaF Concentration but Constant NaF Content on Oral Fluoride Retention"; Caries Research; 18:43-47 (1994).

Featherstone et al., "An in situ model for simultaneous assessment of inhibition of demineralization and enhancement of remineralization"; Journal of Dental Research; 71:804-810(Spec Iss)(Apr. 1992).

Feinmann, "This won't hurt a bit"; The Times; (Sat., Mar. 12, 2005).

Fejerskov et al., "Dental fluorosis—a handbook for health workers"; Munksgaard, Copenhagen (1988).

Fejerskov et al., "The Nature of Mechanisms of Dental Fluorosis in Man"; Journal of Dental Research; 69:692-700 (Spec Iss) (Feb. 1990).

Fejerskov et al., "Posteruptive changes in human dental fluorosis—a histological and ultrastructural study"; Pro Finn Dent. Soc.; 87(4) (1991).

Fejerskov et al., "Fluoride in Dentistry 2nd edition"; Munksgaard, Copenhagen (1996).

Ferrazzano, et al., "Nuove strategie nella prevenzione della carie dentaria:studio sperimentale sui caseino-fosfopeptidi"; Prevenzione Odontostomatologica, Quintessenza Edizioni; 4:15-21, English Abstract (2005).

Ferrazzano et al. "New Strategies in dental caries prevention: experimental study on casein phosphopetide"; European Journal of Paedetric Dentistry; 4:183-187 (2007).

(56) References Cited

OTHER PUBLICATIONS

Ferrazzano et al., "Protective effect of yogurt extract on dental enamel demineralization in vitro"; Australian Dental Journal; 53:314-319 (2008).
Freml, L. et al., "Efficacy of Hypersensitivity Agents on Demineralization under Provisional Crowns"; Abstract 1346, IADR, New Orleans, USA (2007).
Fuller et al., "Efficacy of MI Paste in Preventing Demineralization in Overdenture Abutments"; Abstract 0503, IADR, New Orleans, USA (2007).
Gandolfi et al., "Calcium silicate coating derived from Portland cement as treatment for hypersensitive dentine"; Journal of Dentistry; 36:565-578 (2008).
Giambro et al., "Characterization of Fluorosed Human Enamel by Color Reflectance, Ultrastructure, and Elemental Composition"; Caries Res.; 29:251-257 (1995).
Giniger et al., "A 180-Day Clinical Investigation of the Tooth Whitening Efficacy of a bleaching Gel with Added Amorphous Calcium Phosphate"; Journal of Clinical Dentistry; XVI(1):11-16 (2005).
Giniger et al., "The clinical performance of professionally dispensed bleaching gel with added amorphous calcium phosphate"; JADA; 136:383-392 (2005).
Gugnani et al., "Comparative evaluation of two commercially available desensitising agents after scaling and root planning: an in vivo stud"; PERIO; 5(2):121-129 (2008).
Haderlie et al., "MI Paste and Fluoride effects on Secondary Caries"; Abstract 0504, IADR, New Orleans, USA (2007).
Harper et al., "Cariostatic Evaluation of Cheeses with Diverse Physical and Compositional Characteristics"; Caries Res.; 20:123-130 (1986).
Harper et al., "Modification of Food Cariogenicity in Rats by Mineral-Rich Concentrates from Milk"; J. Dent Res.; 66:42-45 (1987).
Hartshone, "The relationship between plaque index scores, fluoride content of plaque, plaque pH, dental caries experience and fluoride concentration in drinking water in a group of primary school children"; Journal of the Dental Association of South Africa; 49:5-10 (1994).
Hay et al., "A Clinical Trial of the Anticaries Efficacy of Casein Derivatives Complexed with Calcium Phosphate in Patients with Salivary Gland Dysfunction"; Oral. Surg. Oral Med Oral. Pathol Oral Radiol. Endod.; 93:271-275 (2002).
Hicks et al. "Biological factors in dental caries: role of remineralization and fluoride in the dynamic process of demineralization and remineralization (part 3)"; The Journal of Clinical Pediatric Dentistry; 28(3):203-214 (2004).
Hicks et al., "Casein Phosphopeptide-Amorphous calcium phosphate paste: root surface caries formation"; Abstract 3275—IADR, Baltimore, Maryland, USA (Mar. 2005).
Holler et al., "Fluoride uptake and distribution in enamel and dentin after application of different fluoride solutions"; Clin Oral Invest; 6:137-144 (2002).
Holloway et al., "Effects of Various Sucrose-Casein Ratios in Purified Diets on the Teeth and Supporting Structures of Rats"; Arch Oral Biol.; 3:185-200 (1961).
Holt et al., "Ability of a β-casein Phosphopeptide to modulate the precipitation of calcium phosphate by forming amorphous dicalcium phosphate nanoclusters"; Biochem. J.; 314:1035-1039 (1996).
Holt, "An equilibrium thermodynamic model of the sequestration of calcium phosphate by casein micelles and its application to the calculation of the partition of salts in milk"; Euro. Biophysics J.; 5:421-434 (2004).
Huang et al., "Remineralization of eroded teeth using CPP-ACP paste", Abstract 3267, Toronto, Canada. (Jul. 2008).
Huq et al., "A H-NMR study of the casein Phosphopeptide αs1-casein (59-79)"; Biochimica et biophysica Acta; 1247:201-208 (1995).
Huq et al., "Molecular Modeling of the Multiphosphorylated Sequence Motif Bound to Hydroxyapatite Surfaces"; Journal Mol. Mod.; 6:35-47 (2000).
Huq et al., "Nascent Helix in the multiphosphorylated peptide $\alpha_{S2}$-casein(2-20)"; Journal of Peptide Science; 9:386-392, (2003).
Huq et al., "Molecular Modelling of the Multiphosphorylated Casein Phosphopeptide Alpha S1-Casein (59-79) based on NMR constraints"; Journal of Dairy Research; 71:28-32 (2004).
Iijima et al., "Acid Resistance of Enamel Subsurface Lesions Remineralized by a Sugar-Free Chewing Gum Containing Casein Phosphopeptide-Amorphous Calcium Phosphate (CPP-ACP)"; Caries Research; 38:551-556 (2004).
Iijima et al., "Acid resistance of remineralized enamel by a sugar-free chewing gum"; Abstract 184—84th General Session of the IADR, Brisbane, Australia (Jun. 28-Jul. 1, 2006).
Inaba et al. "Effect of Sodium Hypochlorite Treatment on Remineralization of Human Root Dentine in vitro"; Caries Research; 30:218-224 (1996).
Inaba et al. "Intraoral changes in NaOCl—treated Root Dentin Lesions: A Pilot Study"; Journal of Dental Health; 50:824-826 (2000).
Kandelman et al., "A 24-month clinical study of the incidence and progression of dental caries in relation to consumption of chewing gum containing xylitol in school preventive programs"; Journal Dent Res.;69(11):1771-1775 (1990).
Kariya et al., "Fluoride Effect on Acid Resistance Capacity of CPP-ACP Containing Material"; Abstract 2045—82nd General Session of the IADR, Honolulu, Hawaii (2004).
Kariya et al., "Remineralization of enamel lesion by a novel cream with both CPP-ACP and fluoride"; Poster session 136—54th Annual ORCA Congress (2007).
Keçik et al., "Effect of Acidulated Phosphate Fluoride and Casein Phosphopeptide-Amorphous Calcium Phosphate Application on Shear Bond Strength of Orthodontic Brackets"; Angle Orthodontist; 78(1):129-133 (2008).
Khan, "White Spots on Teeth"; Buzzle.com Intelligent Life on the Web (Jan. 2010).
Kim et al., "Remineralization of the artificial caries lesion using CPP-ACP and fluoride"; Abstract 3280, Toronto, Canada. (Jul. 2008).
Kowalczyk et al., "Evaluation of the product based on Recaldent™ technology in the treatment of dentin hypersensitivity"; Advances in Medical Sciences; 51(S 1):40-42, 2006.
Krobicka et al., "The Effects of Cheese Snacks on Caries in Desalivated Rats"; Journal of Dental Research; 66:1116-1119, (1987).
Kumar et al., "The effect of casein phosphopeptide-amorphous calcium phosphate on remineralization of artificial caries-like lesions: an in vitro study"; Australian Dental Journal; 53:34-40 (2008).
Larsson et al. "Fluoride concentration in plaque in adolescents after topical application of different fluoride varnishes"; Clin Oral Invest; 4:31-34 (2000).
Lasfargues et al., "La reminéralisation des lésions carieuses (2) synergies thérapautiques"; Realités Cliniques; 15(3):261-275. English Abstract (2004).
Legeros, "Calcium phosphates in demineralization/remineralization processes"; Journal of Clinical Dentistry; 10:65-73 (1999).
Lewis, "Brush, floss and mousse?"; Women Dentistry Journal; 2(4):18-19 (Winter 2005).
Little et al., "An equilibrium thermodynamicmodel of the sequestration of calcium phosphate by casein phosphopeptides"; Euro Biophysics J.; 33:435-447 (2004).
Loesche, "Role of streptococcus mutans in human dental decay"; Microbiological Reviews; 50(4):353-380 (Dec. 1986).
Lynch et al, "Low-Levels of Fluoride in plaque and saliva and their effect on the demineralization and remineralisation of enamel; role of fluoride of toothpastes"; Int'l Dental Journal; 54(5):304-309 (2004).
Malcmacher,"Vitamins for teeth"; Common Sense Dentistry; pp. 130 and 144 (Oct. 2006).
Malcmacher, "Enamel Remineralization: The Medical Model of Practicing Dentistry"; Dentistry Today; (Nov. 2006).
Manton et al. "In situ remineralisation by sugar-free gums, one containing CPP-ACP"; Abstract 0020—45th Annual Meeting of Australian/New Zealand Division of the IADR (Sep. 25-28, 2005).

(56) References Cited

OTHER PUBLICATIONS

Manton, "Promoting remineralization: using casein phosphopeptide—stabilized amorphous calcium (fluoride) phosphate. A chemical approach." EAPD, Amsterdam (Jun. 8-11, 2006).
Manton et al., "Remineralization of white spot lesions in situ by tooth mousse"; Abstract 185—84th General Session of the IADR, Brisbane, Australia (Jun. 28-Jul. 1, 2006).
Manton et al. "Effect of ozone and Tooth Mousse™ on the efficacy of peroxide bleaching"; Australian Dental Journal; 53:128-132 (2008).
Manton, "Dental Caries: Where to From Here?"; Ann Roy Austral Coll Dent Surg.; 19:73-76 (May-Jun. 2008).
Manton et al., "Remineralization of enamel subsurface lesions in situ by the use of three commercially available sugar-free gums"; International Journal of Paediatric Dentistry; 18:284-290 (2008).
Mazzaoui et al.,"Incorporation of Casein Phosphopeptide-Amorphous Calcium Phosphate into a Glass-ionomer Cement"; Journal of Dental Research; 82(11):914-918 (2003).
Melkers, "Keeping focused on the finish line. Accomplishing goals with traditional and progressive technologies"; Dentaltown; 5(11):60, 62, 64&66 (2004).
Mickenautsch, "An Introduction to Minimal Intervention Dentistry (MI)"; Dental News; XIV(IV):13-20 (2007).
Milnar, "Considering biomodification and remineralization techniques as adjuncts to vital tooth-bleaching regimens"; Compendium; 28(5):234-240 (2007).
Minami et al., "Effects of Cheese and Milk Containing CPP-ACP on Enamel Remineralization"; 2049—82nd General Session of the IADR, Honolulu, Hawaii, Abstract only (2004).
Misra et al. "Early Childhood Caries—A Review"; Dental Update; 34:556-564 (2007).
Miyazaki et al., "Using ultrasound transmission velocity to analyze demineralization of tooth substrate"; Abstract 94—52nd ORCA Congress, Indianapolis, USA / Caries Research, 39:319 (Jul. 2005).
Morgan et al., "CPP-ACP gum slows progression and enhances regression of dental caries"; Abstract 2445—84th General Session of the IADR, Brisbane, Australia (Jun. 28-Jul. 1, 2006).
Morgan et al., "The Anticariogenic Effect of Sugar-Free Gum Containing CPP-ACP Nanocomplexes on Approximal Caries Determined Using Digital Bitewing Radiography"; Caries Research; 42:171-184 (2008).
Morgan et al., "Clinical trial of tooth mousse on white spot lesions"; Cooperative research centre for oral health science. Toronto, Briefing Paper No. 2 (2008).
Morgan et al., "A Clinical Trial Measuring White Spot Lesion Progression and Regression"; Abstract 0112, Toronto, Canada (Jul. 2008).
Moule et al. "Resin bonding using an all-etch or self-etch adhesive to enamel after carbamide peroxide and/or CPP-ACP treatment"; Australian Dental Journal; 52(2):133-137 (2007).
Mount, "A new paradigm for operative dentistry"; Australian Dental Journal; 52(4):264-270 (2007).
Murata et al., "Remineralization Power by Xylitol Chewing Gums"; Abstract 2046—82nd General Session of the IADR, Honolulu, Hawaii. Abstract only (2004).
Narayana model of the sequestration of calcium phosphate by casein micelles and its application to the calculation of the partition of salts in milk et al., "An in vitro study of wear prevention in dentine"; Abstract 2424—84th General Session of the IADR, Brisbane, Australia (Jun. 28-Jul. 1, 2006).
Ng et al. "Aesthetic management of severely fluorosed incisors in an adolescent female"; Australian Dental Journal; 52(3):243-248 (2007).
O'Hehir, "Caries—More than a filling"; Hygienetown Magazine Hygientown.com, pp. 8-12 (Jul./Aug. 2008).
Oshiro et al., "Effect of CPP-ACP paste on tooth mineralization: an FE-SEM study"; Journal of Oral Science; 49(2):115-120 (2007).
Perdigao et al., "Contemporary Trends and Techniques in Tooth Whitening: A Review"; Practical Procedures & Aesthetic Dentistry; 16(3):185-192 (2004).

Perich et al., "Efficient Solution-Phase Synthesis of Multiple O-Phosphoseryl-Containing Peptides Related to Casein and Statherin"; Int. J. Pept. Protein Res.v 40(2):81-88 (Aug. 1992).
Perich et al., "The Use of Synthetic Phosphopeptides for Epitope Mapping of the AS1-Casein Phosphopeptide Segment 59-70"; Bioorg. Med. Chem. Lett.; 2:1153-1154 (1992).
Peschke et al. "Nucleating Ability of Calcium Phosphate-Protein-Composites."; Abstract 2244, IADR, New Orleans, USA (2007).
Piekarz et al. "An in vitro assessment of the role of Tooth Mousse in preventing wine erosion."; Australian Dental Journal; 53:22-25 (2008).
Pietrzycka, "Chemical methods of treatment of dental caries: the action and application of CPP-ACP"; E-Dentico; 2(18):68-74, English Abstract (2008).
Pitts, "Are we ready to move from operative to non-operative/preventive treatment of dental caries in clinical practice?"; Caries Research; 38:294-305 (2004).
Plate et al., "Investigation of the early mineralization on collagen in dentine of rat incisors by quantitative electron spectroscopic diffraction (ESD)"; Cell Tissue Research; 278:543-547 (1994).
Poitevin et al., "Clinical Effectiveness of a CPP-ACP Crème for Tooth Hypersensitivity Treatment"; EADR Istanbul, Abstract 0136 (Aug. 24-28, 2004).
Quartarone et al., "Surface kinetic roughening caused by dental erosion: an atomic force microscopy study"; Journal of Applied Physics; 103(104702):1-6 (2008).
Rahiotis et al. "Effect of a CPP-ACP agent on the demineralization and remineralization of dentine in vitro"; Journal of Dentistry; 35:695-698 (2007).
Rahiotis et al., "Characterization of oral films formed in the presence of a CPP-ACP agent: An in situ study"; Journal of Dentistry; 36:272-280 (2008).
Ramadas, "The oral care for children with malignancies"; Synopses; Synopses: The Newsletter of the Australian and New Zealand Society of Paediatric Dentistry, Winning 2003 Postgraduate Essay; 28:1-20 (Mar. 2004).
Ramalingam et al., "An in Vitro Investigation of the Effects of Casein Phosphopeptide-Stabilized Amorphous Calcium Phosphate (CPP-ACP) on Erosion of Human Dental Enamel by a Sports Drink"; IADR, General Session, San Diego Abstract 2810 (2002).
Ramalingam et al., "Erosion of Human Dental Enamel by Sports Drinks"; Synopses; 27:16-19, (2003).
Ramalingam et al., "Adding Caesin Phosphopeptide-amorphous Calcium Phosphate to Sports Drinks to Elimante In Vitro Erosion"; Pediatric Dentistry; 27(1):61-67 (2005).
Ranjitkar et al., "Enamel wear prevention under conditions simulating bruxism and acid regurgitation"; Abstract 2428—84th General Session of the IADR, Brisbane, Australia (Jun.28-Jul. 1, 2006).
Ranjitkar et al., "The Role of Tooth Mousse in preventing enamel wear"; Poster 0375—session 39—42nd annual meeting of IADR—Continental European and Israeli Divisions, Sep. 26-29, 2007.
Ranjitkar et al., "The role of tooth mousse in reducing erosive tooth wear"; Abstract 2500, Toronto, Canada. (Jul. 2008).
Rees et al., "Pronamel and tooth mousse: An initial assessment of erosion prevention in vitro"; Journal of Dentistry; 35:355-357 (2007).
Reeves, "Calcium Phosphate Sequestering Phosphopeptide from Casein"; Latour NG. Science; 128:472 (1958).
Reich, "Das kleine gewisse Etwas zur Remineralisation"; Zahnmedizin, English Abstract; 95(21):2-9 (2005).
Reich, "Flüssiger Zahnschmelz"; Dental Magazine; English Abstract (Feb. 2005).
Reich, Dental Products Report Europe (Downloaded on May 30, 2006 http://www.dpreurope.com) (Jan. 1, 2006).
Reich, "GC Tooth Mousse—Ein neuer Ansatz zur Remineralisation"; Kongress: Wissenschaft und Praxis der Sanften Zahnheilkunde, Lindau am Bodensee; English Abstract (Mar. 3-4, 2006).
Reich, "Die Betreuung von Kariespatienten in der Praxis"; Quintessenz; 59(12):1301-1307, English Abstract (2008).
Reynolds et al., "A Review of the Effect of Milk on Dental Caries"; Aust. J. Dairy Tech.; 34:175-179 (1979).

(56) References Cited

OTHER PUBLICATIONS

Reynolds et al., "Effect of Milk on Caries Incidence and Bacterial Composition of Dental Plaque in the Rat"; Arch Oral Biol.; 26(5):445-451 (1981).
Reynolds et al., "Phosphoprotein Inhibition of Hydroxyapatite Dissolution"; Calcif. Tissue Int.; 34(S 2):552-6. (1982).
Reynolds et al., "Effect of Adsorbed Protein on Hydroxyapatite Zeta Potential and Streptococcus Mutans Adherence"; Infect. Immun.; 39(3):1285-1290. (Mar. 1983).
Reynolds et al., "Effect of Casein and Whey-Protein Solutions on Caries Experience and Feeding Patterns of the Rat"; Arch Oral Biol.; 29(11):927-33. (1984).
Reynolds et al., "Reduction of Chocolate's Cariogenicity by Supplementation with Sodium Caseinate"; Caries Res.; 21(5):445-51. (1987).
Reynolds et al., "Confectionery Composition and Rat Caries"; Caries Res. 21(6):53-845 (1987).
Reynolds, "The Prevention of Sub-Surface Demineralization of Bovine Enamel and Change in Plaque Composition by Casein in an Intra-Oral Model"; J. Dent. Res.; 66(6):1120-1127. (Jun. 1987).
Reynolds et al., "Protein Dissimilation by Human Salivary-Sediment Bacteria"; J. Dent. Res.; 68:124-29 (1989).
Reynolds et al., "Cariogenicity of a Confection Supplemented with Sodium Caseinate at a Palatable Level"; Caries Res.; 23:368-370 (1989).
Reynolds et al., "A Selective Precipitation Purification Procedure for Multiple Phosphoseryl-Containing Peptides and Methods for Their Identification"; Anal. Biochem.; 217(2):277-284. (Mar. 1994).
Reynolds, "Dairy Products and Dental Health." Proceedings of the Nutrition Society of Australia; 19:95-102 (1995).
Reynolds et al., "Anticariogenicity of Calcium Phosphate Complexes of Tryptic Casein Phosphopeptides in the Rat"; Journal of Dental Research; 74(6):1272-1279 (Jun. 1995).
Reynolds, "Remineralization of Enamel Subsurface Lesions by Casein Phosphopeptide-stabilized Calcium Phosphate Solutions"; J Dent Res; 76(9):1587-1595 (Sep. 1997).
Reynolds, "Dairy products and dental health"; Proc Nutr Soc Aus; 19:95-102 (1995).
Reynolds, "Anticariogenic"; J. of Sp. Care in Dentistry; 18(1):8-16 (1998).
Reynolds et al., "Advances in Enamel Remineralization: Anticariogenic Casein Phosphopeptide-Amorphous Calcium Phosphate"; J. Clin. Dent.; X(2):86-88. (1999).
Reynolds, "Anticariogenic Casein Phosphopeptides"; Prot. Peptide Lett.; pp. 295-303 (1999).
Reynolds, "The Role of Phosphopeptides in Caries Prevention"; Dental Perspectives; 3:6-7. (1999).
Reynolds et al., "Enamel Remineralization by Chewing Gum Containing Casein Phosphopeptide-Amorphous Calcium Phosphate"; IADR, General Session, Chiba, Abstract 0489 (2001).
Reynolds, "Health aspects of dairy products—Dairy products in relation to caries prevention and oral health." Invited review. Encycl Dairy Sciences (2001).
Reynolds, "Remineralization of early enamel caries by anticariogenic casein phosphopeptide-amorphous calcium phosphate nanocomplexes"; Dental Practice (Nov./Dec. 2001).
Reynolds, "Caries Prevention and Oral Health"; Health Aspects of Dairy Products/Caries Prevention and Oral Health, Elsevier Science Ltd, pp. 1306-1313 (2002).
Reynolds, "Dairy Components in Oral Health"; Aust. J. Dairy Tech.; 58:79-81 (2003).
Reynolds et al., "Retention in Plaque and Remineralization of Enamel Lesions by Various Forms of Calcium in a Mouthrinse or Sugar-free Chewing Gum"; Journal of Dental Research; 82(3):206-211 (2003).
Reynolds et al. "Additional Aids to the Remineralisation of Tooth Structure"; Preservation and Restoration of Tooth Structure, Knowledge Books & Software, 8:111-118 (2005).

Reynolds et al., "Improved plaque uptake and enamel remineralization by fluoride with CPP-ACP"; Abstract 2538—84th General Session of the IADR, Brisbane, Australia. (Jun.28-Jul. 1, 2006).
Reynolds, "Calcium phosphate-based remineralization systems: scientific evidence?"; Australian Dental Journal; 53:268-273 (2008).
Reynolds et al. "Fluoride and casein phosphopeptide-amorphous calcium phosphate"; J Dent Res; 87(4):344-348 (2008).
Sudjalim et al., "Prevention of demineralization around orthodontic brackets in vitro"; American Journal of Orthodontics and Dentofacial Orthopedics; 131(6):705.E1-705.E9 (2007).
Roberts, "Role of Models in Assessing New Agents for Caries Prevention—Non-Fluoride Systems"; Adv. Dent. Research; 9(3):304-311; discussion 312-314 (Nov. 1995).
Roberts et al., "Remineralisation of fluorotic enamel lesions by casein phosphopeptide-amorphous calcium fluorophosphate (CPP-ACFP) solution"; IADR, ANZ division, Abstract 54 (2000).
Robinson et al. "Effect of Surface Zone Deproteinisation on the Access of Mineral Ions into Subsurface Carious Lesions of Human Enamel"; Caries Research; 24:226-230 (1990).
Rose, "Binding Characteristics of Streptococcus Mutans for Calcium and Casein Phosphopeptide"; Caries Research; 34:427-431 (2000).
Rose, "Effects of an Anticariogenic Casein Phosphopeptide on Calcium Diffusion in Streptococcal Model Dental Plaques"; Arch Oral Biol; 45(7):569-575 (2000).
Rosen et al., "Effect of Cheese, With and Without Sucrose, on Dental Caries and Recovery of Streptococcus Mutans in Rats"; Journal of Dental Research; 633:894-896 (1984).
Rozwadowska, "Children and private dentistry"; Private Dentistry; Special Issue, pp. 109-113 (May 2006).
Sakaguchi et al., "Preventing acid induced enamel demineralization using CPP-ACP containing paste"; Abstract 2055—IADR, Baltimore, Maryland, USA (Mar. 2005).
Sakaguchi et al., "Remineralization potential of CPP-ACP and its synergy with fluoride", Abstract 191— 84th General Session of the IADR, Brisbane, Australia (Jun. 28-Jul. 1, 2006).
Sato et al., "Caries prevention Potential of a Tooth-coating Material Containing Casein Phosphopeptide-Amorphous Calcium Phosphate (CPP-ACP)"; IADR, General session, Goteborg, Abstract 1007 (2003).
Schüpbach et al., "Incorporation of Caseinoglycomacropeptide and Caseinophosphopeptide into the Salivary Pellicle Inhibits Adherence of Mutans Streptococci"; Journal of Dental Research; 75:1779-1788 (1996).
Schweigert et al., "Dental caries in the cotton rat. VI. The effect of the amount of protein, fat and carbohydrate in the diet on the incidence and extent of carious lesions"; Journal of Nutrition; 31:439-447 (1946).
Shaw, "Effects of dietary composition on tooth decay in the albino rat"; Journal of Nutrition; 41:23-24 (1950).
Sheharyar et al., "Efficacy of MI Paste for Sensitivity Associated With Vital Bleaching"; Abstract 2041, IADR, New Orleans, USA (2007).
Shen et al., "Remineralization of Enamel Subsurface Lesions by Sugar-free Chewing Gum Containing Casein Phosphopeptide-Amorphous Calcium Phosphate"; J Dent Res; 80(12):2066-2070 (2001).
Shen et al., "Enamel remineralization by a mouthrinse containing casein phosphopeptide-amorphous calcium phosphate and fluoride in an in situ model"; Australian Dental Journal ADRF; Special Research Supplement, 49(4):S19 (2004).
Shen et al., "Remineralization by a mouthrinse containing CPP-ACP at pH 5.5"; Abstract 189—84th General Session of the IADR, Brisbane, Australia (Jun. 28-Jul. 1, 2006).
Shen et al. "Remineralization of Enamel"; The Univ. of Melbourne. Research Reports; pp. 266-270.
Silva et al., "Effects of Water-soluble Components of Cheese on Experimental Caries in Humans"; J Dent Res; 66(1):38-41 (Jan. 1987).
Silva et al. "Fluoride content of infant formulae in Australia"; Australian Dental Journal; 41:1 (1996).
Slomiany et al., "Salivary Mucins in Oral Mucosal Defense"; Gen. Pharmac.; 27(5):761-771 (1996).

(56) References Cited

OTHER PUBLICATIONS

Smith et al., "Ultramorphological evaluation of dentin after treatment with different desensitizing agents"; Abstract 0941, IADR, New Orleans, USA (2007).
Smolenski et al., "Mi Paste and Fluoride for Caries Prevention In-Vitro"; Abstract 0505, IADR, New Orleans, USA (2007).
Steinberg, "A modern paradigm for caries management, Part 1: Diagnosis and Treatment"; Dentistry Today (Downloaded on Mar. 1, 2007, http://www.dentistrytoday.net) (Feb. 2007).
Steinberg, "A modern paradigm for caries management, Part 2: A practical protocol"; Dentistry Today (Downloaded on Jul. 1, 2007, http://www.dentistrytoday.net) (Jun. 2007).
Stößer, "Kariesprotektive Eigenschaften des durch Caseinphosphopeptid stabilisierten amorphen Calciumphosphat-Nanokomplexes (CPP-ACP)"; Deutsche Zahnärztliche Zeitschrift; 82 Abstract (Sep. 2007).
Sudjalim et al., "Prevention of white spot lesions in orthodontic practice: a contemporary review", Australian Dental Journal, 51(4):284-289 (2006).
Sukasaem et al., "Effect of CPP-ACP on hardness of enamel eroded by Cola-drink." Abstract 1673—84th General Session of the IADR, Brisbane, Australia (Jun. 28-Jul. 1, 2006).
Talbo et al., "MALDI-PSD-MS Analysis of the Phosphorylation Sites of Caseinomacropeptide"; Petides; 22(7):1093-1098. (Jul. 2001).
Takamizawa et al., "Determination of demineralization of tooth substrate by use of an ultrasonic device"; Japan J Conserv Dent; 47(24) Spring Issue—Abstract B-4, (Jun. 2004).
Tantbirojn et al., "Changes in surface hardness of enamel by a cola drink and CPP-ACP paste"; Journal of Dentistry; 36:74-79 (2008).
Ten Cate, "Current concepts on the theories of the mechanism of action of fluoride"; Acta Odontol, Scand; 57 (1999).
Theerapiboon et al., "Remineralization of artificial caries by CPP-ACP paste"; Abstract 3274, Toronto, Canada. (Jul. 2008).
Trajtenberg et al., "CPP-ACP Paste with Fluoride: In Vitro Root Surface Caries Formation"; Abstract 0500, IADR New Orleans, USA (2007).
Turssi et al., "Progression of erosion following use of calcium and phosphorus compounds"; Abstract 2499, Toronto, Canada. (Jul. 2008).
Ung et al., "Investigation of the binding of casein phosphopeptides to the major enamel pellicle proteins"; Australian Dental Journal ADRF; Special Research Supplement, 49(4):S19-S20 (2004).
Vladic et al., "Combined CPP-ACP and photoactivated disinfection (PAD) therapy in arresting root surface caries: a case report"; British Dental Journal; 203(8):457-459 (2007).
Walker et al., "Increased remineralization of tooth enamel by milk containing added casein phosphopeptide-amorphous calcium phosphate"; Journal of Dairy Research; 73:74-78 (2006).
Walsh et al., "Effect of CPP-ACP versus potassium nitrate on cervical dentinal hypersensitivity"; Abstract 947—84th General Session of the IADR, Brisbane, Australia. (Jun.-Jul. 1, 2006).
Walsh, "The effects of GC Tooth Mousse on cervical dentinal sensitivity: a controlled clinical trial"; International Dentistry SA—Australasian Edition; 5(1):16-23 (2007).
Walsh, "Application of the System for Total Environmental Management (STEM) to demineralization, dental erosion and tooth wear"; Australasian Dental Practice, pp. 52-58 (Jan.-Feb. 2008).
Weiss, "Kariesprophylaxe in der kinderzahnärztlichen Praxis"; ZWP; 18:76-79. English Abstract (Oct. 2005).
Westerman et al., "Argon Laser and Remineralizing Paste Effect on Root Surface Caries"; Abstract 0018, IADR, New Orleans, USA (2007).
Westerman et al., "The Argon Laser and Remineralizing Paste with Fluoride Effects on Enamel Caries"; AAPD,Washington (2008).
White, "Use of Synthetic Polymer Gels for Artificial Carious Lesion Preparation"; Caries Research; 21:228-242. Abstract Only (1987).
Wilfershausen et al., "In-Vitro—Studie Zur Überprüfung einermöglichen Remeralisation durch caesinphosphopetidhaltige Calciumphosphat-komplexe (CPP__ACP)"; Deutsche Zahnärztiche Zeitschrift; 63(2):134-139. English Abstract.
William et al., "Molar Incisor Hypomineralization: Review and Recommendations for Clinical Management"; Pediatric Dentistry; 28(3):224-232 (2006).
Wong et al., "Incorporation of casein phosphopeptide-amorphous calcium phosphate into a temporary cement"; Abstract 0653—84th General Session of the IADR, Brisbane, Australia (Jun. 28-Jul. 1, 2006).
Wong et al., "Plaque microcosm biofilm mineralization by CPP-ACP and calcium-phosphate-monofluorophosphate-urea mineralizing solution"; Abstract 1269—84th General Session of the IADR, Brisbane, Australia (Jun. 28-Jul. 1, 2006).
Wright et al., "Artificial Caries Inhibited with MI Paste and Two Restorative Materials"; Abstract 2777, IADR, New Orleans, USA (2007).
Xie et al., "Remineralization Effects of CPP-ACP and Proanthocyanidin on Artificial Root Caries"; Abstract 0512, IADR, New Orleans, USA (2007).
Yamaguchi et al., "Effect of CPP-ACP paste on mechanical properties of bovine enamel as determined by an ultrasonic device"; Journal of Dentistry, 34:230-236 (2006).
Yamaguchi et al., "Ultrasonic determination of the effect of casein phosphopeptide-amorphous calcium phosphate paste on the demineralization of bovine dentin"; Caries Research; 41:204-207 (2007).
Zero, "In situ caries models"; Advance Dent Research; 9(3):214-230, discussion 231-234 (Nov. 1995).
Zhang et al. "Experimental study of phosphopeptide in promoting tooth remineralisation"; Chinese Journal of Dental Research; 3(1):27-30 (May 2000).
Zhao et al. "The Remineralization for Enamel lesions by Casin Phosphopeptide-Amorphous Calcium phospate in vitro"; Zhonghua Kou Qiang Yi Kxue Za Zhi; 36(6):421-423 (2002).
Caplus Copyright 2005. "NMR Studies of a Novel Calcium, Phosphate and Fluoride Delivery Vehicle <SYM97>$_{S1}$-Casein (59-79) by Stabilized Amorphous Calcium Fluoride Phosphate Nanocomplexes".
"Caséin phosphopeptide et phosphate de calcium amorphe: un complexe prometteur", Dialogue Dentaire; 30:27-29 (Spring 2005). English Abstract provided.
"Colorimetry", CIE Technical Committee, Second Edition, CIE 1986.
Database WPI Week 200316, Thomason Scientific, London, GB; 2003-165149, XP002537968 & SE 0 100 558 A, Mediteam Dental AB, Abstract (Aug. 21, 2002).
"Editors' Choice—Prospec MI Paste"; The Dental Advisor; 22(5) (Jun. 2005).
"GC stellt Kasein-haltige Zahnschutzcreme vor—Vorbeugen statt reparieren"; DZW Special IDS-Nachlese; English Abstract (2005).
"GC Tooth Mousse—Eine ganz andere Art der Prävention"; Dental Spiegel; pp. 53-54. English Abstract (Feb. 2005).
"Minimale Intervention für maximale Mundgesundheit"; DZW Special; English Abstract (Mar. 2005).
"Minimum Intervention: modernes Kariesmanagement— Weg vom chirurgichen, hin zum medizinischen Versorgungsansatz mit GC. IDS-31$^{st}$ International Dental Show"; Cologne, (Today—Independent Trade Show Daily—Saturday) (Apr. 12-16, 2005).
"Preventive agents"; The Dental Advisor; 21(10):1-5 (Dec. 2004).
"Preventative Agents", The Dental Advisor 21(13) (Dec. 2004).
"Products for the dental hygienist—Desensitizers"; The Dental Advisor, 23(6) (Jul./Aug. 2006).
"Putting mouths where the money is"; DPRAsia (Jan./Feb. 2007).
"Tooth Mousse: Pierre qui roule n'amasse pas mousse? Ben si!"; Clinic—27:218 (Apr. 2006)—English Abstract provided.
"Tradition und modernes know how—ein Erfolgsrezept"; Zahn Prax ; 5:267 English Abstract (2005).
Translation of Russian Office Action from Application No. 2007123603, May 26, 2009.
International Search Report and Written Opinion for related PCT/AU2006/000885 mailed Sep. 25, 2006.

* cited by examiner

STABILIZED CALCIUM PHOSPHATE COMPLEXES

RELATED APPLICATIONS

This application is a Continuation Application of U.S. Ser. No. 11/720,285, filed 25 May 2007, now U.S. Pat. No. 8,609,071, issued 17 Dec. 2013, which is a National Stage Application of PCT/AU2005/00017819, filed 24 Nov. 2005, which claims benefit of Ser. No. 2004906762, filed 25 Nov. 2004 in Australia and which applications are incorporated herein by reference. To the extent appropriate, a claim of priority is made to each of the above disclosed applications.

The present invention relates to amorphous calcium phosphate and/or amorphous calcium fluoride phosphate stabilised by phosphopeptides. Methods of making the complexes of the invention and of treatment or prevention of dental caries. Dental calculus, dental erosion/corrosion and dental hypersensitivity are provided. These have anticariogenic properties, protecting tooth structures as they remineralise (repair) early stages of dental caries, as well as other dental/medical applications (including anti-calculus, anti-erosion/corrosion and anti-dentinal hypersensitivity).

BACKGROUND

Dental caries is initiated by the demineralisation of hard tissue of the teeth usually by organic acids produced from fermentation of dietary sugar by dental plaque odontopathogenic bacteria. Dental caries is still a major public health problem. Further, restored tooth surfaces can be susceptible to further dental caries around the margins of the restoration.

Even though the prevalence of dental caries has decreased through the use of fluoride in most developed countries, the disease remains a major public health problem. Dental erosion/corrosion is the loss of tooth mineral by dietary or regurgitated acids. Dental hypersensitivity is due to exposed dentinal tubules through loss of the protective mineralized layer, cementum and dental calculus is the unwanted accretion of calcium phosphate minerals on the tooth surface. All these conditions, dental caries, dental erosion/corrosion, dental hypersensitivity and dental calculus are therefore imbalances in the level of calcium phosphates.

Dental caries, dental erosion/corrosion and dental hypersensitivity can be treated with stabilized amorphous calcium phosphate (ACP) or stabilized amorphous calcium fluoride phosphate (ACFP) by providing bioavailable calcium and phosphate ions to replace the lost calcium phosphate mineral. Stabilized ACP and stabilised ACFP can also bind to the surface of dental calculus and prevent or reduce further accretion. Stabilized ACP and stabilized ACFP therefore can play a major role in preventing and treating oral diseases and other medical conditions.

Casein is present in milk in the form of micelles, which are believed to be roughly spherical particles with a radius of about 100 nm, dispersed in a continuous phase of water, salt, lactose and whey proteins (Schmidt, D. G. (1982) *Dev. Dairy Chem.* 1, 61-86). The casein micelles serve as a carrier of calcium phosphate providing a bioavailable source of calcium and phosphate ions for bone and teeth formation. The ability of casein micelles to maintain calcium and phosphate ions in a soluble and bioavailable state is retained by multiphosphorylated peptide fragments of the caseins known as the casein phosphopeptides (CPP). WO 98/40406 in the name of The University of Melbourne describes casein phosphopeptide-amorphous calcium phosphate complexes (CPP-ACP) and CPP-stabilised amorphous calcium fluoride phosphate complexes (CPP-ACFP) which have been produced at alkaline pH. Such complexes have been shown to prevent enamel demineralisation and promote remineralisation of enamel subsurface lesions in animal and human in situ caries models (Reynolds, 1998)

The CPP which are active in forming the complexes do so whether or not they are part of a full-length casein protein. Examples of active (CPP) that can be isolated by tryptic digestion of full length casein have been specified in U.S. Pat. No. 5,015,628 and include peptides Bos $\alpha_{s1}$-casein X-5P (f59-79) [1], Bos β-casein X-4P (f1-25) [2], Bos $\alpha_{s2}$-casein X-4P (f46-70) [3] and Bos $\alpha_{s2}$-casein X-4P (f1-21) [4] as follows:

[1]
Gln$^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-Lys$^{79}$ $\alpha_{s1}$(59-79)

[2]
Arg$^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-Arg$^{25}$ β(1-25)

[3]
Asn$^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-Lye$^{70}$ $\alpha_{s2}$(46-70)

[4]
Lys$^{1}$-Asn-Thr-Met-Glu-His-Val-Ser(P)-Ser(P)-Ser(P)-Glu-Glu-Ser-Ile-Ile-Ser(P)-Gln-Glu-Thr-Tyr-Lys$^{21}$ $\alpha_{s2}$(1-21)

It has now been found that peptide-stabilized soluble, basic forms of ACP and ACFP may also be produced in a medium having a pH of less than 7.0. Such complexes demonstrate a surprising level of activity to remineralise enamel subsurface lesions of teeth.

It will also be understood that the term "comprises" (or its grammatical variants) as used in this specification is equivalent to the term "includes" and may be used interchangeably and should not be taken as excluding the presence of other elements or features.

SUMMARY OF THE INVENTION

In one aspect, the present invention provides a phosphopeptide (PP) stabilized-ACP or ACFP complex, wherein the complex is formed at a pH of below 7.0. Preferably the complex is formed at a pH in the range of about 5.0 up to but below 7.0. More preferably the complex is formed at a pH range of about 5.0 to about 6.0. In a preferred embodiment, the complex is formed at a pH of about 5.5. In a preferred embodiment, the complex is suitable for dental applications. In a further preferred embodiment, the complex is suitable for application to the teeth and/or gums to promote remineralisation.

By "formed at a pH of" is meant that the medium in which the complex is formed has an overall pH of the defined value. The localized pH values within the medium may vary, for example in the microenvironment around the forming complex. In other words, the relevant pH value for the purposes of the present invention is the measurable pH of the medium as a whole.

Preferably, the phase of the ACP is predominantly a basic phase, wherein the ACP comprises predominantly the species $Ca^{2+}$, $PO_4^{3-}$ and $OH^-$. The basic phase of ACP may have the general formula $[Ca_3(PO_4)_2]_x[Ca_2(PO_4)(OH)]$ where $x \geq 1$.

Preferably, the phase of the ACFP is predominantly a basic phase, wherein the ACFP comprises predominantly the species $Ca^{2+}$, $PO_4^{3-}$ and $F^-$. The basic phase of ACFP may have the general formula $[Ca_3(PO_4)_2]_x[Ca_2(PO_4)F]_y$ where $x \geq 1$ when $y=1$ or where $y \geq 1$ when $x=1$ It is believed that, structurally, the ACP in the PP stabilised ACP complex of the present invention contains a hydroxide anion in place of the fluoride anion in ACFP.

"Phosphopeptide" in the context of the description of this invention means an amino acid sequence in which at least 2 amino acids are phosphorylated. At least two of the phospho-amino acids in the sequence are preferably contiguous. Preferably the phosphopeptide includes the sequence A-B-C-D-E, where A, B, C, D and E are independently phosphoserine, phosphothreonine, phosphotyrosine, phosphohistidine, glutamic acid or aspartic acid, and at least two, preferably three, of the A, B, C, D and E are phosphoamino acids. In one embodiment, the phosphoamino acid residues are phosphoserine, for example three contiguous phosphoserine residues. In a preferred embodiment, the phosphopeptide includes three contiguous phosphoserine residues followed by two glutamic acid residues in a sequence represented as Ser(P)-Ser(P)-Ser(P)-Glu-Glu (where Ser(P) is phosphoserine and Glu is glutamic acid).

In one embodiment, the PP is a casein phosphopeptide (CPP) which is intact casein or a fragment of casein. Thus, the PP can be a casein phosphoprotein or a polyphosphopeptide. The complex formed may have the formula $[CPP(ACP)_8]_n$ or $[(CPP)(ACFP)_8]_n$ where n is equal to or greater than 1, for example 6. The complex formed may be a colloidal complex, where the core particles aggregate to form small (e.g. about 2-5 nm) and large (eg about 100 nm) colloidal particles suspended in water.

The PP may be from any source; it may be present in the context of a larger polypeptide, including a full length casein polypeptide, or it may be isolated by tryptic or other enzymic digestion or by chemical hydrolysis (for example by alkali or acid) of casein or other phosphoamino acid rich proteins such as phosphitin, or by chemical or recombinant synthesis, provided that it comprises the sequence A-B-C-D-E, as defined above. The sequence flanking this core sequence may be any sequence. However, those flanking sequences in $\alpha_{s1}(59-79)$ [1], $\beta(1-25)$ [2], $\alpha_{s2}(46-70)$ [3] and $\alpha_{s2}(1-21)$ [4] are preferred. The flanking sequences may optionally be modified by deletion, addition or conservative substitution of one or more residues. The amino acid composition and sequence of the flanking region are not critical.

In a preferred embodiment, the PP is one or more casein phosphopeptides selected from the group consisting of $\alpha_{s1}$ (59-79) [1], $\beta(1-25)$ [2], $\alpha_{s2}(46-70)$ [3] and $\alpha_{s2}(1-21)$ [4].

Without being bound by any theory or mode of action, it is believed that the PP binds to the ACP or ACFP cluster to produce a metastable complex which exists in solution. This binding is believed to inhibit the growth of ACP or ACFP to a size that initiates nucleation and precipitation of calcium phosphate. In this way, calcium and other ions such as fluoride ions can be localised, for instance at a surface on a tooth to prevent demineralisation and prevent formation of dental caries. It is therefore believed that this provides a mechanism for delivering amorphous calcium phosphate in a bioavailable form that is able to remineralise teeth.

In a further embodiment, the invention provides a stable ACFP complex or a stable ACP complex as described above, which complex acts as a delivery vehicle that co-localises ions including, but not limited to calcium, fluoride and phosphate ions at a target site. In a preferred embodiment, the complex includes calcium phosphate in an amorphous form that produces superior anti-caries anti-erosion/corrosion, anti-calculus and anti-dental hypersensitivity efficacy. The target site is preferably teeth or bone.

In a further aspect the present invention provides a phosphopeptide stabilised amorphous calcium phosphate (ACP) or amorphous calcium fluoride (ACFP) complex, wherein the complex is formed at a pH of 7.0 or below, and wherein the ACP or ACFP is predominantly in a basic form.

For the avoidance of doubt, the phosphopeptide stabilized ACP or ACFP complexes of the present invention exclude complexes formed at a pH of above 7.0 as described in WO 98/40406.

The complexes are preferably substantially free of ions other than calcium, phosphate, fluoride and hydroxide ions, although they do contain water molecules. The complexes are also preferably formulated with PP such that they are soluble in water. In the context of the present invention, the term "soluble" also includes the situation where the complexes may also be described as being in a colloidal dispersion.

In one embodiment, the ACP complex consists essentially of PP, calcium, phosphate and hydroxide ions and water.

In one embodiment, the ACFP complex consists essentially of PP, calcium, phosphate, fluoride and hydroxide ions and water.

In a further aspect, the invention also provides a method of producing a stable complex of ACP as described above, comprising the steps of:

(i) obtaining a solution comprising at least one phosphopeptide and;

(ii) admixing solutions comprising calcium ions, phosphate ions and hydroxide ions, while maintaining the pH at about 7.0 or below.

In a preferred embodiment of this aspect of the present invention, the hydroxide ions are titrated into the solution to maintain the phosphopeptide solution at an essentially constant pH. In a further preferred embodiment, the calcium and phosphate ions are titrated into the phosphopeptide solution with constant mixing and at a rate that avoids the formation of a calcium phosphate precipitate in the phosphopeptide solution.

In a further aspect, the invention also provides a method of producing a stable complex of ACFP as described above, comprising the steps of:

(i) obtaining a solution comprising at least one phosphopeptide and;
(ii) admixing solutions comprising calcium ions, phosphate ions, hydroxide ions and fluoride ions, while maintaining the pH at about 7.0 or below.

In a preferred embodiment of this aspect of the present invention, the hydroxide ions are titrated into the solution to maintain the phosphopeptide solution at an essentially constant pH. In a further preferred embodiment, the calcium, phosphate and fluoride ions are titrated into the phosphopeptide solution with constant mixing and at a rate that avoids the formation of a calcium phosphate precipitate in the phosphopeptide solution.

The pH may be adjusted by the addition of hydrogen ions (acid) or hydroxide ions (base) as required.

Any physiologically compatible or acceptable acid may be used a source of hydrogen ions that does not attack the complexes themselves. Typically, hydrochloric acid will be used. Any physiologically acceptable base, eg NaOH, may be used as a source of hydroxide ions to adjust the pH and to otherwise supply hydroxide ions as required for the formation of the complex. The exact acids and bases used are not considered critical subject to the above.

In a preferred embodiment, high concentrations of calcium ions and phosphate ions (for example 3 M calcium ions and 1 M phosphate ions) are titrated into the phosphopeptide solution used in the method of producing a stable ACP complex or the method of producing a stable ACFP complex according to the present invention. Preferably, the solutions of calcium ions and phosphate ions are added very slowly in aliquots (for example around 1% volume addition per minute) with thorough mixing. In a preferred embodiment, an aliquot of the phosphate ion solution is added before an aliquot of calcium ion solution. The hydroxide ions are preferably added continually. In a preferred embodiment, the hydroxide ions are added after each calcium ion addition.

In a further aspect of the invention there is provided a method of producing a phosphopeptide stabilised amorphous calcium phosphate (ACP) complex comprising the steps of
(i) obtaining a solution comprising at least one phosphopeptide and;
(ii) admixing solutions comprising calcium ions, phosphate ions and hydroxide ions while maintaining the pH at about 7.0 or below.

In a further aspect of the invention there is provided a method of producing a phosphopeptide stabilised amorphous calcium fluoride phosphate (ACFP) complex comprising the steps of
(i) obtaining a solution comprising at least one phosphopeptide and;
(ii) admixing solutions comprising calcium ions, phosphate ions and hydroxide ions while maintaining the pH at about 7.0 or below.

In a further aspect of the invention there is provided a formulation comprising a phosphopeptide stabilized ACP or ACFP complex wherein the pH of the formulation is less than 7.0. In one embodiment, the pH of the formulation is between about pH 5.0 and up to but below pH 7.0. Preferably the pH of the formulation is between about pH 5.0 and about 6.0. In a preferred embodiment, the pH of the formulation is about 5.5.

Thus, the phosphopeptide-stabilized ACP or ACFP complex may be formed at a pH of about 7.0 and below, and then placed in an environment having a different pH, preferably a pH of between 4 and 10. In one embodiment the pH is between 4.5 and 6.5, more preferably between 5 and 6, and most preferably about 5.5.

The complexes of the invention are useful as calcium supplements in subjects in need of stimulation of bone growth, for example subjects undergoing fracture repair, joint replacement, bone grafts, or craniofacial surgery. These complexes are also useful as dietary supplements in subjects who for any reason, such as dietary intolerance, allergy, or religious or cultural factors, are unable or unwilling to consume dairy products in an amount sufficient to supply their dietary calcium requirements.

Embodiments of the invention are described below in which the environment for the complexes may be a formulation for a particular purpose, such as exemplified below. The pH of this environment may be adjusted as set out above for optimal effect, regardless of the pH at which the complex was originally formed, given the stability of the complexes formed.

In one embodiment, there is provided a method for remineralising teeth comprising applying to the teeth a complex as described above, desirably in a pharmaceutically acceptable carrier. The complex may contain ACP, ACFP or both. The method is preferably applied to a subject in need of treatment.

In one preferred embodiment of the invention, the stable ACFP or ACP complex is incorporated into oral compositions such as toothpaste, mouth washes or formulations for the mouth to aid in the prevention and/or treatment of dental caries or tooth decay. The ACFP or ACP complex may comprise 0.01-50% by weight of the composition, preferably 1.0-50%. For oral compositions, it is preferred that the amount of the PP-ACP and/or PP-ACFP administered is 0.01-50% by weight, preferably 1.0%-50% by weight of the composition. In a particularly preferred embodiment, the oral composition of the present invention contains about 2% PP-ACP, PP-ACFP or a mixture of both. The oral composition of this invention which contains the above-mentioned agents may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. The oral composition according to this invention may further include additional well known ingredients depending on the type and form of a particular oral composition.

In certain preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 5 to about 9 and typically from about 5.0 to 7.0. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In one embodiment, the oral composition according to the present invention has a pH of about 5.5 and contains stable ACP or ACFP.

In other desirable forms of this invention, the oral composition may be substantially solid or pasty in character, such as toothpowder, a dental tablet or a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 cm$^2$/g, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner, for example as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in an amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed.

Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The invention also provides use of a composition as described above. In the preferred practice of this invention an oral composition according to this invention such as mouthwash or dentifrice containing the composition of the present invention is preferably applied regularly to the gums and teeth, such as every day or every second or third day or preferably from 1 to 3 times daily, at an acidic pH, preferably of about 4.5 to about 7.0, for at least 2 weeks up to 8 weeks or more up to a lifetime. In one embodiment, the pH of the oral composition is about 5.0, 5.5, 6.0, 6.5 or 7.0.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like.

In another embodiment, the complex of the invention is formulated to form a dietary supplement preferably comprising 0.1-100% w/w, more preferably 1-50% w/w, most preferably 1-10% and particularly 2% w/w of a comestible. The complex may also be incorporated into food products.

In a further aspect, the invention provides compositions including pharmaceutical compositions comprising any of the ACFP and/or ACP complexes as described above together with a pharmaceutically-acceptable carrier. Such compositions may be selected from the group consisting of dental, anticariogenic compositions, therapeutic compositions and dietary supplements. Dental compositions or therapeutic compositions may be in the form of a gel, liquid, solid, powder, cream or lozenge. Therapeutic compositions may also be in the form of tablets or capsules. In one embodiment, the ACP and/or ACFP complexes are substantially the only remineralising active components of such a composition.

The invention further includes a formulation described above provided together with instructions for its use to treat or prevent any one or more of dental caries or tooth decay, dental erosion/corrosion, dentinal hypersensitivity and dental calculus.

According to a further aspect of the invention there is provided a composition for dental restoration, including a dental restorative material to which has been added an ACFP and/or ACP complex according to the present invention. The base of the dental restorative material can be a glass ionomer cement, a composite material or any other restorative material which is compatible. It is preferred that the amount of CPP-ACP complex or CPP-ACFP complex included in the dental restorative material is 0.01-80% by weight, preferably 0.5-10% and more preferably 1-5% by weight. The dental restorative material of this invention which contains the above mentioned agents may be prepared and used in various forms applicable to dental practice. The dental restorative material according to this embodiment may further include other ions, eg. antibacterial ions $Zn^{2+}$, $Ag^+$, etc or other additional ingredients depending on the type and form of a particular dental restorative material. It is preferable that the pH of dental restorative material according to this embodiment be between 2-10, more preferably 5-9 and even more preferably 5-7. It is preferable that the pH of the dental restorative material containing the CPP-ACP complex or ACFP complex be in the range of about 2 to 10, more preferably in the range of about 5 to 9 and even more preferably in the range of about 5 to 7.

The invention is also directed to a method of manufacture of a restorative composition. Preferably, the method includes the addition of an ACP and/or ACFP complex as described above, to a base dental restorative material. The invention also relates to use of a restorative composition as stated above for the treatment and/or prevention of dental caries.

The invention also relates to a kit of parts including (a) dental restorative material and (b) CPP-ACP complex or CPP-ACFP complex together with instructions for their use for the preparation of a composition containing a complex described above for dental restoration.

The invention also relates to a kit of parts including (a) dental restorative material (b) casein phosphopeptide (c) calcium ions and (d) phosphate ions, and (e) hydroxide ions and optionally fluoride ions, together with instructions for their use for the preparation of a composition for dental restoration.

In a further aspect, there is provided a method of treating or preventing one or more of each of dental caries or tooth decay, dental erosion/corrosion, dentinal hypersensitivity and dental calculus comprising the step of administering a complex or composition of the invention to the teeth or gums of a subject, preferably one in need of such treatments. Topical administration of the complex is preferred. The method preferably includes the administration of the complex in a formulation as described above.

The invention also provides a method of treatment and/or prevention of dental caries, dental erosion/corrosion, dental hypersensitivity and dental calculus in animals including providing the dental restorative composition according to the invention, or manufactured according to the invention, and applying to teeth in an animal in need of treatment and/or prevention.

In a further aspect, the invention relates to methods of treating one or more conditions related to calcium loss from the body, especially from the bones, calcium deficiency, calcium malabsorption, or the like. Examples of such conditions include, but are not limited to, osteoporosis and osteomalacia. In general any condition which can be improved by increased calcium bioavailability is contemplated.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

The invention will now be described with reference to the following non-limiting examples.

EXAMPLE 1

Preparation of CPP-ACFP and CPP-ACP Solutions

Stock solutions of 3.25M $CaCl_2$, 1.25 M $Na_2HPO_4$, 1M NaOH and 1M NaF were added in approximately thirty aliquots to a 10-15% w/v tryptic digest of casein until a final concentration of approximately 78 mM $Ca^{2+}$, 48 mM phosphate and 12 mM fluoride concentrations were obtained. The solutions were added slowly (that is, less than approximately 1% volume addition per minute). An aliquot of the phosphate solution was added first, followed by an aliquot of the calcium solution. The pH was maintained at 7.0, 6.5, 6.0, 5.5 and 5.0 using the NaOH with thorough mixing. The sodium hydroxide solution was added automatically by a pH stat with the addition of the hydroxide ions usually being after each addition of the calcium ions. After addition of the calcium ions, phosphate ions, hydroxide ions and fluoride ions the solution was filtered through a 0.1 micron filter to concentrate 1-2 fold. The retentate may be washed with water to remove salts and inactive (and bitter tasting) peptides if desired. CPP-ACP solutions were prepared as above without the addition of fluoride.

At the completion of each titration and filtration a sample of each retentate was taken and less than 10% collected as a filtrate using a 3000 molecular weight cut-off Centriprep 3 ultrafiltration membrane. The Centripreps containing the samples were centrifuged at 1,000 g for 15 min in a Beckman J2-21 centrifuge using a JA 10.5 rotor. The original sample before Centriprep centrifugation and a sample of the filtrate after Centriprep centrifugation were taken for analysis of calcium, phosphate and fluoride concentrations. The analysis of the original sample gave total calcium, phosphate and fluoride ion concentrations and the analysis of the filtrate gave free (unbound) calcium, phosphate and fluoride concentrations. The difference between the total and unbound concentrations is the bound concentration of Ca, Pi and F by the CPP and that is presented in Table 1 and Table 2.

In a first illustration of an embodiment of the invention, bound calcium, phosphate and fluoride of 2% CPP-ACFP were measured in complexes prepared at acidic pH values, as shown in Table 1.

TABLE 1

| pH | Ca mM | Phosphate mM | F mM | Molar Ratio Ca:P:F |
|---|---|---|---|---|
| 7.0 | 75.9 ± 1.7 | 45.6 ± 1.3 | 10.8 ± 0.4 | 7.0:4.2:1 |
| 6.5 | 73.6 ± 1.7 | 44.2 ± 1.4 | 10.8 ± 0.4 | 6.8:4.1:1 |
| 6.0 | 69.4 ± 1.8 | 41.8 ± 1.3 | 10.9 ± 0.4 | 6.4:3.9:1 |
| 5.5 | 59.6 ± 1.8 | 34.6 ± 2.0 | 10.9 ± 0.4 | 5.5:3.2:1 |
| 5.0 | 41.2 ± 2.3 | 23.6 ± 1.6 | 11.3 ± 0.4 | 3.7:2.1:1 |

In a second illustration of an embodiment of the invention, bound calcium and phosphate of 2% CPP-ACP were measured in complexes prepared at acidic pH values, as shown in Table 2.

TABLE 2

| pH | Ca mM | Phosphate mM | Molar Ratio Ca:P |
|---|---|---|---|
| 7.0 | 61.9 ± 1.1 | 37.5 ± 1.8 | 1.7:1 |
| 6.5 | 58.8 ± 1.1 | 36.0 ± 1.6 | 1.6:1 |
| 6.0 | 52.6 ± 1.3 | 32.8 ± 1.8 | 1.6:1 |
| 5.5 | 43.1 ± 1.4 | 27.1 ± 1.6 | 1.6:1 |
| 5.0 | 23.0 ± 2.6 | 13.4 ± 1.7 | 1.7:1 |

The results of this experiment demonstrate that nanocomplexes or nanoclusters of amorphous calcium phosphate and amorphous calcium fluoride phosphate stabilised by casein phosphopeptides (CPP) are formed at acidic pH, as they are retained after the filtration step due to aggregation at high concentrations. The ratios of bound calcium and phosphate and fluoride of Table 1 and 2 demonstrate that the complexes formed contain basic amorphous calcium phosphate and basic amorphous calcium fluoride phosphate (ACFP). The basic ACP phase was $[Ca_3(PO_4)_2]_x[Ca_2(PO_4)(OH)]$ where x=1-2 for all pH values. The basic ACFP phase was $[Ca_3(PO_4)_2]_x[Ca_2(PO_4)F]_y$ where x=1 and y=1-2 (pH 5.0) and where y=1 and x=1-2 (pH 5.5-7.0). Also, it can be seen that the amount of calcium ions and phosphate ions bound at acidic pH remains relatively high until the pH of formation drops to the region of about 5.0.

It is believed, without being bound by any theory or mode of action, that the formation of the complexes can be achieved at acidic pH by the steady addition of OH anions, such as by NaOH addition, preferably with agitation, such that the OH anions with the calcium ions and phosphate ($PO_4^{3-}$) ions form basic ACP sufficiently for it to be stabilised by the CPP, which then drives the reaction to form more ACP upon further OH addition. Moreover, in the case of ACFP, the F permits a lower pH environment for complex formation, and it can be seen from Table 1 that a greater amount of calcium is bound in ACFP complexes at a given acidic pH than ACP at the same pH.

EXAMPLE 2

Comparison of Remineralization of Enamel Subsurface Lesions In Vitro by CPP-ACP and CPP-ACFP at Acidic pH Values The polished enamel surface of extracted human third molars were sawn as a slab (8×4 $mm^2$) and covered with acid resistant nail varnish to form an occlusal-half and a gingival-half mesiodistal window (1×7 $mm^2$) separated by 1 mm. The protocol used for the comparison was that described in Reynolds (1997) Remineralization of enamel subsurface lesions by casein phosphopeptide-stabilized calcium phosphate solutions. *J Dent Res* 76:1587-1595, which is known to one skilled in the art, and the contents of which are incorporated herein by reference. Subsurface enamel lesions were created on these windows using the Carbopol method of White (described Reynolds, 1997). The enamel slabs were sawn in half to 4×4 $mm^2$ blocks. The gingival-half lesion on one block and the occlusal-half lesion on the other block were sealed with varnish to create the demineralized controls.

The enamel half-lesions were exposed to the different remineralization solutions for 10 days at 37° C. without mixing. The remineralization solutions were 2% CPP-ACP or 2% CPP-ACFP prepared at pH 7.0, 6.5, 6.0, 5.5 and 5.0 and maintained in solutions having the respective pH of formation.

After remineralization each pair of blocks was dehydrated in ethanol and embedded in methyl-methacrylate resin (Paladur, Kulzer, Germany). Three 200-300 μm sections were cut perpendicular to the lesion surface, lapped down to 80±5 μm and radiographed beside an aluminium stepwedge of 10×14 μm thick increments as described previously (Shen at al., 2001, J. Dent. Res. 80:2066-2070), the entire contents of which are incorporated herein by reference.

Radiographic images of the lesions were viewed via transmitted light through a Dilux 22 microscope (Ernst Leitz Wetzlar, Germany). The images were acquired by video camera (Sony DXC 930P) and digitized (Scion imaging corporation, colour grabber 7) under the control of imaging software (Optimas 6.2). Images of the lesions, controls and the aluminium stepwedge were scanned as previously described by Shen et al. (2001). The enamel section thickness was measured and volume percentage mineral data determined using the equation of Angmar (1963) as previously described by Shen at al. (2001). The percentage remineralization (% R) was also calculated as previously described by Shen et al. (2001).

The remineralization of the enamel subsurface lesions by these solutions is shown in Table 3.

TABLE 3

| pH | Percentage Enamel Remineralization (% R) | |
|---|---|---|
| | CPP-ACFP | CPP-ACP |
| 7.0 | 17.6 ± 4.8 | 15.0 ± 3.5 |
| 6.5 | 20.8 ± 5.8 | 19.9 ± 6.1 |
| 6.0 | 30.7 ± 8.7 | 27.7 ± 8.4 |
| 5.5 | 57.7 ± 8.5 | 41.8 ± 8.5 |
| 5.0 | 40.0 ± 11.2 | 18.4 ± 9.2 |

The results of Table 3 demonstrate that 2% CPP-ACP and CPP-ACFP solutions remineralise enamel subsurface lesions at substantial levels, notwithstanding the acidic pH values. Both CPP-ACP and CPP-ACFP produced optimal remineralization at pH 5.5. Even at pH 5.0 where normally enamel demineralization would otherwise occur, 2% CPP-ACP produced 18% remineralization and 2% CPP-ACFP produced 40% remineralization demonstrating the superior properties of CPP-ACFP in acidic solutions.

EXAMPLE 3

Comparison of Enamel Remineralisation In Situ by CPP-ACP at pH 7.0 and 5.5

This study was a double-blind and crossover design to assess the ability of a mouthrinse containing 0.5% w/v CPP-ACP prepared and maintained at pH 5.5 compared with a mouthrinse containing 0.5% w/v CPP-ACP prepared and maintained at pH 7.0 to enhance enamel remineralization in an intraoral model. Approval for the study was obtained from The University of Melbourne Human Research Ethics Committee and the Royal Dental Hospital of Melbourne Ethics in Clinical Research Committee. Four healthy adult subjects (2 males and 2 females) were recruited from the staff and postgraduate students (age 21 to 47 years) of the School of Dental Science. All subjects had at least 22 natural teeth with no current caries activity, periodontal disease or other oral pathology. None of the subjects were using antibiotics or medications, which could have affected salivary flow rate. The unstimulated salivary flow rate of each subject was in excess of 0.2 ml/min. Unstimulated salivary flow rates were measured by instructing the subjects to lean forward with their heads tilted downwards, allowing saliva to flow into a pre-weighed centrifuge tube for exactly 2 min. Stimulated salivary flow rates were measured by instructing the subjects to consume sugar-free chewing gum for exactly 2 min while allowing all saliva produced to flow into a pre-weighed centrifuge tube.

Removable mid-palatal acrylic appliances covering the first premolars to the last tooth in the arch were fabricated for each subject as described previously (Shen et al., 2001).

Extracted human third molars were obtained from the Royal Dental Hospital of Melbourne. Any extracted soft tissues were removed and the teeth were stored in an 18% v/v formalin acetate solution. Sound, relatively planar buccal and lingual surfaces free of cracks, stains and fluorosis (as viewed under a dissecting microscope) were selected and thrice rinsed with Milli-Q water. The outer enamel surface was removed and polished wet to a mirror finish using Soflex™ (3M) discs on a slow speed contra-angle dental handpiece. Each polished surface was then sawn from the tooth as an approximately 8×4 mm slab, using a water-cooled diamond blade saw and the whole slab covered with acid-resistant nail varnish except for two (occlusal and gingival) mesiodistal windows (1×7 mm) separated from each other by 1 mm. Lesions were created in the enamel windows by mounting each slab onto the end of a 3-4 cm stick of yellow dental sticky wax and immersing in 40 ml of unagitated demineralization buffer, consisting of 20 g/l Carbopol 907™ (carboxypolymethylene, BF Goodrich, Cleveland, Ohio), 500 mg/l hydroxyapatite (Bio-Gel® HTP, Bio-Rad Laboratories, Richmond, CL), and 0.1 mol/l lactic acid (Ajax Chemicals, Auburn, NSW) pH 4.8, for 4 days at 37° C. A change of solution was made after 2 days at which time the slabs were removed from the solution, rinsed thrice with Milli-Q water, blotted dry and placed into fresh demineralization buffer. The slabs were similarly rinsed and dried after four days of demineralization. This demineralization procedure produced consistent subsurface lesions of approximately 80-100 μm depths (LDd) with intact surface layers, as evaluated by microradiography of sections of the artificial lesions. After demineralization each enamel slab was sawn through the midline of each window into two 4×4 mm half-slabs and the cut surface of each half-slab covered with nail varnish. One half-slab of each pair was retained as the demineralization control and stored in a labelled 1.5 ml microcentrifuge tube together with a drop of Milli-Q water, thereby creating a humidified environment. The other enamel half-slab of the pair was inset into an intraoral appliance and retained using dental wax for the remineralization protocol. Care was taken to keep the windows free of wax. Four enamel half-slabs were inset into each appliance, two on each side in bilateral troughs (Shen et al., 2001).

The test mouthrinses contained 0.5% w/v CPP-ACP prepared as described in Example 1 at pH 5.5 or pH 7.0. The products were provided as coded products. The code was not released until all the data had been acquired. This study utilized a double blind, cross-over design with two treatments: (i) a mouthrinse containing 0.5% (w/v) CPP-ACP at pH 7.0, and (ii) a mouthrinse containing 0.5% (w/v) CPP-ACP at pH 5.5. Subjects were randomly assigned to each of the mouthrinses.

At the commencement of the study all subjects were provided with an adequate supply of a standard fluoride dentifrice which they were instructed to use for the duration of the study. Subjects were instructed to brush their teeth with a fluoride dentifrice early morning and bedtime. They were also instructed to rinse their mouths with water before insertion of the intra-oral appliance. Subjects wore removable palatal appliances with four human-enamel half-slabs inset containing subsurface demineralized lesions. Each subject was instructed to rinse with 5 ml of mouthrinse for 60 seconds as soon as the appliance was inserted into the mouth. The subjects continued to wear the appliance for another 40 minutes. This was done 4 times a day for 10 consecutive days at the following times: 10:00 am; 11:30 am; 2:00 pm and 3:30 pm. While the appliance was being worn, the subjects were instructed not to eat or drink anything. Following the 10 day testing period, there was a one-week washout period. The subjects then crossed over to the other treatments. When the appliance was removed from the mouth, it was briefly rinsed with Milli-Q water and kept in a sealed moist plastic bag and stored in at room temperature. Subjects were informed not to brush the area containing the enamel blocks. Subjects kept a diary of product use and appliance wearing times. No alterations were made to the subjects' diet or oral hygiene procedures for the duration of the study. After each treatment period the enamel half-slabs were removed, paired with their respective demineralized control enamel half-slabs, embedded, sectioned and subjected to microradiography and computer-assisted densitometric image analysis to determine the level of remineralization.

After each treatment, the enamel half-slabs were paired with their respective control half-slabs and then dehydrated in absolute alcohol. Each pair of half-slabs was embedded, sectioned and subjected to microradiography and computer-assisted densitometric analysis as described by Shen et al. (2001). Radiographic images of the lesions and the neighbouring areas of sound enamel were scanned using the program's line luminance function that gives readings in gray values between 0 and 256. Each lesion was scanned six times through an area free of artefacts or cracks. Each scan comprised 200 readings taken from the tooth surface through the lesion to sound enamel. An aluminium stepwedge image on each slide was scanned and the averaged step grey value readings were plotted against aluminium thickness. The readings of the tooth section image lay within the linear portion of the stepwedge curve and linear regression was used to convert the grey value data into values of equivalent thickness of aluminium. The section thickness was measured and the vol % mineral data computed using the equation of Angmar at al. (1963) and the linear absorption coefficients of aluminium, organic matter plus water and apatitic mineral (131.5, 11.3 and 260.5 respectively). The image of the median strip between the two lesions was scanned six times and averaged to give a control densitometric profile of sound enamel. The lesion images (treated windows and demineralization control windows) to the gingival and occlusal side of the median strip were similarly scanned, as close as possible to the median strip but avoiding any irregularities commonly found at the lesion edges, and the % mineral profiles were computed.

The vol % mineral profile of each enamel half-slabs demineralized and treated lesion was compared with the median sound enamel vol % mineral profile of the same section. The difference between the areas under the densitometric profile of the demineralized control lesion and the median sound enamel, calculated by trapezoidal integration, is represented by $\Delta Zd$. The difference between the areas under the densitometric profile of the treated lesion and the median sound enamel, calculated by trapezoidal integration, is represented by $\Delta Zr$. These parameters were then converted to % change values after treatment, as such, % mineral change (% MC) represents the % change in $\Delta Z$ values:

$$\% \ MC = \frac{\Delta Zd - \Delta Zr}{\Delta Zd} \times 100.$$

Data for the three treatments was statistically tested using analysis of variance (ANOVA) for a randomized complete block design (Norusis M. 1993). Homogeneity of variance was confirmed using Levene's test and normality of the data was confirmed using normal probability plots and the Kolmogorov-Smirnov test. All statistical analyses were performed using SPSS version 11.0 software (Norusis M. 1993).

On obtaining the complete data set of enamel remineralization values the code was released and the decoded data was analyzed. The results in Table 4 represent the mean % MC values for the 4 subjects and the data for each subject obtained from 12 scans (6 each from the gingival and occlusal lesions) performed on each section from the four enamel half-slabs in each appliance. Use of the mouthrinse containing 0.5% (w/v) CPP-ACP at pH 5.5 produced 14.16±1.90% remineralization of the enamel subsurface lesions whereas use of the mouthrinse containing 0.5% (w/v) CPP-ACP at pH 7.0 resulted in only 10.31±2.28% enamel subsurface remineralization. This difference was statistically significant (p<0.01). These data show that CPP-ACP formed at pH 5.5 has 37% greater enamel remineralisation efficacy in situ than CPP-ACP formed at pH 7.0 thus confirming the in vitro results obtained in Example 3.

TABLE 4

Remineralization of enamel subsurface lesions in situ by a mouthrinse containing 0.5% (w/v) CPP-ACP at pH 7.0 or pH 5.5.

| Treatment | $\Delta Zd$ | LDd | $\Delta Zd - \Delta Zr$ | % MC |
|---|---|---|---|---|
| 0.5% CPP-ACP (pH 5.5) | 1726 ± 368 | 100.5 ± 9.1 | 246.2 ± 68.2 | 14.2 ± 1.99 (37%)[a] |
| 0.5% CPP-ACP (pH 7.0) | 1104 ± 340 | 82.4 ± 10.4 | 115.4 ± 46.0 | 10.3 ± 2.3 |

[a]Percentage increased remineralisation over pH 7.0 mouthrinse

EXAMPLE 4

In this example, a number of formulations are provided to exemplify the ways in which complexes of the invention may be formulated for different purpose compositions as described more generally above. These are only examples of the type of formulations that may be provided using various embodiments of the invention.

Toothpaste formulations containing CPP-ACP or CPP-ACFP

Formulation 1

| Ingredient | % w/v |
|---|---|
| Sorbitol | 22.0 |
| Irish Moss | 1.0 |
| Gantrez | 19.0 |
| Purified water | balance |
| Sodium monofluorophosphate | 0.76 |
| Sodium saccharine | 0.3 |
| Pyrophosphate | 2.0 |
| Hydrated alumina | 47.0 |
| Flavour | 0.95 |

-continued

| Ingredient | % w/v |
|---|---|
| CPP-ACP (prepared at pH 5.5) | 2.0 |
| Sodium lauryl Sulphate | 2.0 |
| pH adjusted to 5.5 with NaOH | |

Formulation 2

| Ingredient | % w/v |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl Sulphate | 1.5 |
| Sodium lauryl sarconisate | 0.5 |
| Flavour | 1.0 |
| Sodium saccharine | 0.1 |
| Sodium monofluorophosphate | 0.3 |
| Chlorhexidine gluconate | 0.01 |
| Dextranase | 0.01 |
| CPP-ACFP (prepared at pH 5.5) | 2.0 |
| Purified water | balance |
| pH adjusted to 5.5 with phosphoric acid | |

Formulation 3

| Ingredient | % w/v |
|---|---|
| Sorbitol | 22.0 |
| Irish moss | 1.0 |
| Gantrez | 19.0 |
| Purified water | balance |
| Sodium saccharin | 0.3 |
| Pyrophosphate | 2.0 |
| Hydrated alumina | 48.0 |
| Flavour | 0.95 |
| CPP-ACFP (prepared at pH 5.5) | 2.0 |
| Sodium lauryl Sulphate | 2.0 |
| pH adjusted to 5.5 with NaOH | |

Formulation 4

| Ingredient | % w/v |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl Sulphate | 1.5 |
| Sodium lauryl sarconisate | 0.5 |
| Flavour | 1.0 |
| Sodium saccharine | 0.1 |
| Chlorhexidine gluconate | 0.01 |
| Dextranase | 0.01 |
| CPP-ACFP (prepared at pH 5.5) | 2.0 |
| Purified water | balance |
| pH adjusted to 5.5 with phosphoric acid | |

Formulation 5

| Ingredient | % w/v | |
|---|---|---|
| | 1 | 2 |
| Sorbitol | 58.0 | 58.0 |
| Silica (Zeodent 119) | 20.0 | 20.0 |
| Purified water | balance | balance |
| Sodium lauryl Sulphate | 4.0 | 4.0 |

-continued

| Ingredient | % w/v | |
|---|---|---|
| | 1 | 2 |
| CPP-ACP (prepared at pH 5.5) | 2.0 | — |
| CPP-ACFP (prepared at pH 5.5) | — | 2.0 |
| Sodium dihydrogen phosphate | 1.45 | 1.45 |
| Flavour | 1.0 | 1.0 |
| Sodium carboxymethyl cellulose | 0.75 | 0.75 |
| Titanium dioxide (Rutile) | 0.525 | 0.525 |
| Xanthan gum | 0.475 | 0.475 |
| Sodium saccharin | 0.350 | 0.350 |
| Sodium fluoride | 0.243 | — |
| pH adjusted with phosphoric acid/NaOH | 5.5 | 5.5 |

Formulation 6

| Ingredient | % w/v | |
|---|---|---|
| | 1 | 2 |
| Sorbitol (70% solution) | 31.0 | 31.0 |
| Purified water | balance | balance |
| Silica | 22.0 | 22.0 |
| Glycerol | 8.0 | 8.0 |
| Sodium lauryl Sulphate | 4.0 | 4.0 |
| Polyethylene glycol 300 | 1.0 | 1.0 |
| Sodium fluoride | 0.243 | — |
| Titanium dioxide (Rutile) | 0.525 | 0.525 |
| Xanthan gum | 0.475 | 0.475 |
| Sodium carboxymethyl cellulose | 0.5 | 0.5 |
| Sodium saccharine | 0.286 | 0.286 |
| Sodium acid pyrophosphate | 2.4 | 2.4 |
| Tetra sodium pyrophosphate | 2.2 | 2.2 |
| Flavour | 1.0 | 1.0 |
| CPP-ACP (prepared at pH 5.5) | 2.0 | — |
| CPP-ACFP (prepared at pH 5.5) | — | 2.0 |
| pH | 5.5 | 5.5 |
| pH adjusted with phosphoric acid/NaOH | 5.5 | 5.5 |

Mouthwash Formulations

Formulation 1

| Ingredient | % w/v |
|---|---|
| Ethanol | 10.0 |
| Flavour | 1.0 |
| Sodium saccharin | 0.1 |
| Sodium monofluorphosphate | 0.3 |
| Chlorhexidine gluconate | 0.01 |
| Lauroyl diethanolamide | 0.3 |
| CPP-ACP (prepared at pH 5.5) | 0.5 |
| Water | balance |
| pH adjusted to 5.5 using phosphoric acid/NaOH | |

Formulation 2

| Ingredient | % w/v |
|---|---|
| Gantrez S-97 | 2.5 |
| Glycerine | 10.0 |
| Flavour oil | 0.4 |
| Chlorhexidine gluconate | 0.01 |
| Lauroyl diethanolamide | 0.2 |

-continued

| Ingredient | % w/v |
|---|---|
| CPP-ACFP (prepared at pH 5.5) | 0.5 |
| Water | balance |
| pH adjusted to 5.5 using phosphoric acid/NaOH | |

Lozenge Formulation

| Ingredient | % w/v |
|---|---|
| Sugar/sugar alcohol | 75-80 |
| Corn syrup | 1-20 |
| Flavour oil | 1-2 |
| CPP-ACFP (prepared at pH 5.5) | 0.5-2.0 |
| Mg stearate | 1-5 |
| Water | balance |
| pH adjusted to 5.5 using phosphoric acid/NaOH | |

Chewing Gum Formulation

| Ingredient | % w/v |
|---|---|
| Gum base | 30 |
| Calcium carbonate | 2.0 |
| Crystalline sorbitol | 53.0 |
| Glycerine | 0.5 |
| Flavour oil | 0.1 |
| CPP-ACP (prepared at pH 5.5) | 1.0 |
| Water | balance |
| pH adjusted to 5.5 using citric acid | |

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A composition for dental restoration comprising a phosphopeptide stabilised amorphous calcium phosphate (ACP) or amorphous calcium fluoride phosphate (ACFP) complex, wherein the complex is formed at a pH of from about 5.0 up to but below 7.0, and wherein the ACP or ACFP complex has bound and unbound calcium, wherein the bound calcium in the complex is less than the bound calcium in an ACP or ACFP complex formed at a pH of 7.0 and the ACP or ACFP is predominantly in a basic form.

2. A composition according to claim 1, further comprising a dental restorative material.

3. A composition according to claim 2, wherein the dental restorative material is dental cement.

4. A composition according to claim 3, wherein the dental cement is a glass ionomer cement.

5. A composition according to claim 1, wherein the phosphopeptide stabilised amorphous calcium phosphate (ACP) or amorphous calcium fluoride phosphate (ACFP) complex is in an amount of 0.5 to 10% by weight of the composition.

6. A composition according to claim 1, wherein the phosphopeptide stabilised amorphous calcium phosphate (ACP) or amorphous calcium fluoride phosphate (ACFP) complex is in an amount of 1 to 5% by weight of the composition.

7. A composition according to claim 1, wherein the phosphopeptide includes the sequence Ser(P)-Ser(P)-Ser(P)-Glu-Glu wherein Ser(P) is phosphoserine and Glu is glutamic acid.

8. A composition according to claim 1, wherein the phosphopeptide is a casein phosphopeptide.

9. A composition according to claim 1, wherein the composition is in the form of a dentifrice, tooth gel, mouthwashes, trouches, dental pastes, gingival massage creams, gargle tablets, or other substantially liquid composition prior to application.

10. A composition according to claim 9, wherein the phosphopeptide stabilised amorphous calcium phosphate (ACP) or amorphous calcium fluoride phosphate (ACFP) complex is about 2% by weight of the composition.

11. A composition according to claim 1, wherein the composition is in the form of a mouthwash or mouthrinse.

* * * * *